United States Patent [19]

Oda

[11] Patent Number: 5,780,275
[45] Date of Patent: Jul. 14, 1998

[54] COUPLED PROCESS OF SACCHARIDE FERMENTATION AND MICROBIAL ESTERIFICATION

[75] Inventor: Shinobu Oda, Hiratsuka, Japan

[73] Assignee: Kansai Paint Co., Ltd., Hyogo-Ken, Japan

[21] Appl. No.: 708,965

[22] Filed: Sep. 6, 1996

[30] Foreign Application Priority Data

Sep. 7, 1995 [JP] Japan .................................. 7-254532
Sep. 7, 1995 [JP] Japan .................................. 7-254534

[51] Int. Cl.⁶ .............................. C12P 7/62; C12P 7/40; C12P 7/02; C12N 11/00
[52] U.S. Cl. .......................... 435/135; 435/136; 435/139; 435/140; 435/141; 435/155; 435/158; 435/160; 435/161; 435/174; 435/177; 435/180
[58] Field of Search ...................... 435/41, 134, 174, 435/177, 180, 136, 139, 140, 141, 155, 158, 160, 161

[56] References Cited

PUBLICATIONS

Oda, et al., Journal of Fermentation and Bioengeering, vol. 78, No. 2, 1994, pp. 149–154.
Oda, et al., Biosci. Biotech. Biochem., vol. 56, No. 12 1992, pp. 2041–2045.
Oda, et al., Bioschi. Biotech. Biochem., vol. 56, No. 9, 1992, pp. 1515–1517.

Primary Examiner—David M. Naff
Attorney, Agent, or Firm—Wenderoth, Lind & Ponack, L.L.P.

[57] ABSTRACT

A process is provided for coupled microbial saccharide fermentation and esterification to produce an esterified fermentation product from a saccharide. A microorganism capable of fermenting a saccharide to produce a water-soluble organic acid, alcohol or acetylcoenzyme A, and capable of producing an esterase or alcohol acetyltransferase is attached to a hydrophilic carrier to immobilize the microorganism. The immobilized microorganism is contacted with a hydrophobic organic solvent having dissolved therein a water-insoluble alcohol, organic acid or aldehyde. The organic solvent at an interface is in contact with an aqueous medium containing a saccharide. The microorganism is grown at the interface to ferment the saccharide and produce a water-soluble organic acid, alcohol or acetylcoenzyme A. The esterase or alcohol acetyltransferase produced by the microorganism causes the water-soluble organic acid, alcohol or acetylcoenzyme A to undergo an esterification reaction with the water-insoluble alcohol or organic acid in the organic solvent or with a water-insoluble organic acid produced by microbial oxidation of the water-insoluble alcohol in the organic solvent or with a water-insoluble alcohol or organic acid produced by microbial oxidation of the water-insoluble aldehyde in the organic solvent to a produce an esterified fermentation product from the saccharide.

14 Claims, No Drawings

COUPLED PROCESS OF SACCHARIDE FERMENTATION AND MICROBIAL ESTERIFICATION

BACKGROUND OF THE INVENTION

1. Field of the Invention

This invention relates to a coupling process of fermentation and microbial transformation reaction in which a water-soluble organic acid, alcohol or acetylcoenzyme A fermentatively produced from a saccharide such as glucose is subjected to a microbial esterification reaction.

2. Description of the Related Art

In recent years, the production of substances by microbial transformation is being attempted all over the world. As an application of such microbial transformation, a large number of processes for synthesizing esters by the reverse reactions of hydrolytic enzymes such as lipases and esterases have been proposed, especially for purposes of optical resolution [T. Sugai and H. Ohta, Agric. Biol. Chem., 55, 293 (1991); H. Kakeya, et al., Agric. Biol. Chem., 55, 1877 (1991); T. Sugai and H. Ohta, Agric. Biol. Chem., 54, 3337 (1990)]. In order to cause esterification reactions catalyzed by such enzymes to proceed efficiently, it is necessary to decrease the amount of water present in the reaction system. Accordingly, these enzyme reactions are generally carried out in organic solvents.

Meanwhile, commercially available lipases and esterases are not only expensive, but also have many disadvantage in that it is impossible to esterify the tertiary hydroxyl group, it is difficult to esterify carboxylic acids highly subject to steric hindrance, $\alpha,\beta$-unsaturated carboxylic acids, and carboxylic acids having a substituted aromatic ring, and optical resolution is difficult in the esterification of a primary hydroxyl group having relatively good symmetry. Moreover, if a low-molecular-weight organic acid or alcohol used for esterification is added to the reaction system at high concentrations, the reaction system may show a drop in pH or suffer an inactivation of the lipase or esterase present therein. Accordingly, it is very difficult to synthesize esters at high concentrations [B. Cambou and A. M. Klibanov, Biotechnol. Bioeng., 26, 1449 1984)].

In order to overcome the above-described disadvantages of such commercially available lipases and esterases, the screening of microorganisms capable of producing a novel lipase or esterase and microbial transformation processes utilizing such microorganisms directly as biocatalysts have been extensively attempted. However, since microorganisms are generally destroyed or unable to grow in organic solvents, it is difficult to cause such esterification reactions to proceed stably.

Furthermore, the formation of esters by alcohol acetyltransferase is also known. However, attention has been focused solely on the formation of fragrant esters (isoamyl acetate) in sake, and no investigation made with a view to synthesizing useful esters has been reported.

In contrast, interface bioreactors in which a microorganism attached to a hydrophilic carrier containing nutrients and water and grown at an interface with a hydrophobic organic solvent exhibiting essentially no toxicity to the microorganism is utilized as a biocatalyst can be applied to almost all types of microorganisms and microbial reactions. Thus, they enable esterification reactions to proceed very efficiently [S. Oda and H. Ohta, Biosci. Biotech. Biochem., 56, 2041 (1992); S. Oda, et al., J. Ferment. Bioeng., 78, 149 (1994); Japanese Patent Laid-Open No. 344896/'93]. However, toxicity arising from hydrophilic toxic substances cannot be avoided in interface bioreactors, so that it is difficult to add low-molecular-weight organic acids and alcohols to the reaction system at high concentrations [S. Oda and H. Ohta, Biosci. Biotech. Biochem., 56, 1515 (1992)].

The present inventor made intensive investigations with a view to solving the above-described various problems of the prior art. As a result, it has now been found that they can be solved by coupling fermentation with a microbial esterification reaction through effective utilization of a great feature of an interface bioreactor (namely, its ability to cultivate microorganisms in organic solvents) and the fermentation activity of microorganisms, i.e., by fermentatively producing a water-soluble organic acid, alcohol or acetylcoenzyme A as a precursor thereof while successively subjecting the water-soluble organic acid, alcohol or acetylcoenzyme A to a microbial esterification reaction with a water-insoluble or slightly water-soluble alcohol or organic acid, and while optionally producing the water-insoluble or slightly water-soluble alcohol or organic acid used for the microbial esterification reaction in situ by microbial oxidation of an alcohol or by microbial reduction or oxidation of an aldehyde. The present invention has been completed on the basis of this finding.

SUMMARY OF THE INVENTION

Thus, according to the present invention, there is provided a coupling process of fermentation and microbial transformation which comprises attaching a microorganism having organic acid fermentation activity, alcohol fermentation activity or acetylcoenzyme A fermentation activity and having the ability to produce a lipase, an esterase or an alcohol acetyltransferase to a hydrophilic immobilizing carrier, and bringing a hydrophobic organic solvent containing at least one compound selected from the group consisting of water-insoluble or slightly water-soluble (hereinafter referred to collectively as "hardly water-soluble") alcohols, organic acids and aldehydes into contact with the microorganism on the carrier in the presence of an aqueous medium containing a saccharide serving as a nutrient for the microorganism and as a fermentation material so as to grow the microorganism at the contact interface, whereby a water-soluble organic acid, alcohol or acetylcoenzyme A (hereinafter referred to briefly as "acetyl-CoA") is fermentatively produced from the fermentation material by the action of the grown microorganism and, at the same time, this fermentation product is subjected to a microbial esterification reaction with the hardly water-soluble alcohol or organic acid contained in the hydrophobic organic solvent, with a hardly water-soluble organic acid produced by microbial oxidation of the hardly water-soluble alcohol contained in the hydrophobic organic solvent, or with a hardly water-soluble alcohol or organic acid produced by microbial reduction or oxidation of the aldehyde contained in the hydrophobic organic solvent.

DESCRIPTION OF THE PREFERRED EMBODIMENTS

According to the present invention, the microorganism growing at the solid-liquid interface between the carrier and the hydrophobic organic solvent in an interface bioreactor fermentatively produces a low-molecular-weight water-soluble organic acid, alcohol or acetyl-CoA by utilization of a fermentation material comprising a hydrophilic saccharide such as glucose, starch or sucrose. By the enzymatic action of the lipase, esterase or alcohol acetyltransferase possessed by the microorganism, the resulting fermentation product is esterified with the hardly water-soluble alcohol or organic acid contained in the hydrophobic organic solvent, or with the hardly water-soluble alcohol or organic acid produced in situ by microbial oxidation of the hardly water-soluble alcohol contained in the hydrophobic organic solvent or by microbial reduction or oxidation of the aldehyde contained in the hydrophobic organic solvent, so that a large amount of the esterification product is accumulated in the hydrophobic organic solvent. In this case, the low-molecular-weight water-soluble organic acid, alcohol or acetyl-CoA produced by organic acid fermentation, alcohol fermentation or acetyl-CoA fermentation is successively subjected to an esterification reaction before a concentration at which toxicity or feedback inhibition is developed in the carrier is reached. Consequently, the fermentation product does not exhibit toxicity to the microorganism. Moreover, on the basis of the toxicity alleviation phenomenon at the solid-liquid interface which constitutes a great feature of an interface bioreactor, the addition concentration of the hardly water-soluble alcohol, organic acid or aldehyde contained in the hydrophobic organic solvent and/or the accumulation concentration of the hardly water-soluble alcohol or organic acid produced by the microbial transformation reaction can be markedly increased as compared with the prior art. Furthermore, on the basis of the aforesaid toxicity alleviation phenomenon, the ester produced by the esterification can also be accumulated at a concentration level which is far higher than in the prior art.

When a water-soluble organic acid is produced by fermentation, the above-described microbial esterification reaction causes this organic acid to be esterified with the hardly water-soluble alcohol contained in the hydrophobic organic solvent or the hardly water-soluble alcohol produced by microbial reduction of the hardly water-soluble aldehyde contained in the hydrophobic organic solvent. When a water-soluble alcohol is produced by fermentation, the above-described microbial esterification reaction causes this alcohol to be esterified with the hardly water-soluble organic acid contained in the hydrophobic organic solvent or the hardly water-soluble organic acid produced by microbial oxidation of the hardly water-soluble alcohol or aldehyde contained in the hydrophobic organic solvent.

On the other hand, when acetyl-CoA is produced by fermentation, the acetyl-CoA serves as an acetyl donor for esterifying the hardly water-soluble alcohol contained in the hydrophobic organic solvent or the hardly water-soluble alcohol produced by microbial reduction of the hardly water-soluble aldehyde contained in the hydrophobic organic solvent.

Thus, a first feature of the present invention is that, by utilizing the growth of a microorganism in an organic solvent according to a feature of the interface bioreactor, the microorganism is allowed to produce a water-soluble organic acid, alcohol or acetyl-CoA and, at the same time, this fermentation product is successively subjected to an esterification reaction by the action of the microorganism. In the domain of biotechnology, fermentation and microbial transformation have conventionally been entirely different fields of research or application and, therefore, research or application in each field has been developed quite independently. Consequently, no attempt has been made to couple fermentation with microbial transformation. However, according to the present invention in which a water-soluble organic acid, alcohol or acetyl-CoA is produced by fermentation and, at the same time, this fermentation product is successively subjected to an esterification reaction, the coupling of fermentation with microbial esterification reactions can be achieved in a state favorable to microorganisms.

A second feature of the present invention is that the water-soluble organic acid, alcohol or acetyl-CoA used for esterification can be prevented from developing toxicity to the microorganism or feedback inhibition. Water-soluble organic acids, alcohols and acetyl-CoA develop strong toxicity to microorganisms or feedback inhibition. Accordingly, when they are added to microbial reaction systems according to the prior art, their addition concentrations must be kept low. This unavoidably results in a low reaction rate and a low yield. Moreover, commercially available acetyl-CoA salts are so expensive that it is practically impossible to use them as acetyl donors. In the present invention, however, the water-soluble organic acid, alcohol or acetyl-CoA produced by fermentation is successively subjected to an esterification reaction before a concentration at which toxicity to the microorganism or feedback inhibition is reached. Consequently, the water-soluble organic acid, alcohol or acetyl-CoA does not present the problem of toxicity or feedback inhibition development, making it possible to continue the fermentation and the esterification reaction (as well as the microbial reduction or oxidation reaction) stably.

A third feature of the present invention is that the addition concentration of the hardly water-soluble alcohol or organic acid contained in the hydrophobic organic solvent and used for esterification or of the hardly water-soluble alcohol or aldehyde contained in the hydrophobic organic solvent and used for a microbial reduction or oxidation reaction, or the accumulation concentration of the transformation product, can be kept high owing to the toxicity alleviation phenomenon in the interface bioreactor. The addition concentration of the raw material is a very important factor in the improvement of productivity and yield and, moreover, in the separation and purification of the product, and hence contributes greatly to a reduction in production cost.

A fourth feature of the present invention is that, since the water-insoluble ester being formed migrates spontaneously to the reaction solvent layer of the interface bioreactor, it is possible to avoid the toxicity of the ester and achieve a shift of the reaction equilibrium to esterification, improve the reaction rate, and the like. Moreover, when the hardly water-soluble alcohol, organic acid or aldehyde used as a substrate is highly toxic, such a substrate can be gradually added at low concentrations according to the fed-batch addition method. The accumulation of a high concentration of the resulting ester in the reaction solvent, together with the third feature, contributes greatly to a reduction in production cost.

A fifth feature of the present invention is that, when the concentration of the hydrophilic saccharide is increased in order to achieve efficient fermentative production, side reactions (e.g., microbial oxidation reactions) induced by the growing microorganism and proceeding in parallel with the esterification reaction can be repressed effectively. It is known that the activity of alcohol dehydrogenase catalyzing microbial oxidation reactions is generally inhibited by high concentrations of saccharides (e.g., glucose) [U. Lutstrof and R. Magnet, Arch. Biochem. Biophys., 126, 933 (1968); B. S. Yadav, et al., J. Ferment. Technol., 57, 244 (1979)]. Accordingly, when high concentrations of saccharides are used in the present invention for the purpose of enhancing fermentation activity, microbial oxidation reactions as side reactions are repressed at the same time, resulting in a marked improvement in the yield of the ester produced. On the other hand, when an organic acid is produced by the microbial oxidation of a hardly water-soluble alcohol or aldehyde, the production of an ester can be efficiently achieved by maintaining the concentration of glucose at 2 to 3%.

The interface bioreactor usable in the coupling method of the present invention can be one which is known per se. With regard to the material, size and form of the hydrophilic immobilizing carriers used, the reaction solvents which can be used, and the like, reference may be made, for example, to Japanese Patent Laid-Open No. 91878/'93.

Specific examples of the hydrophilic immobilizing carriers include plate-like structures made of natural polymers such as alginate, carrageenan, starch matrix, agar and cellulosic materials (e.g., filter pads); synthetic polymers such as polyvinyl alcohol, urethane polymers, polyacrylamide and polyacrylic acid; and inorganic porous materials such as foam glass plates. Where it is intended to regenerate and use the carriers repeatedly, it is preferable to use plate-like structures made of a gel-like synthetic polymer or an inorganic porous material. Moreover, in order to impart strength thereto, it is preferable to use a tough porous plate (such as filter pad or foam glass plate) or a plate or bar of stainless steel or the like as a skeleton for the carriers.

The hydrophobic organic solvent used as the reaction solvent should preferably be one having essentially no toxicity to the immobilized microbial cells. Specific examples thereof include normal paraffins or liquid paraffins typified by hydrocarbons of the methane series having 6 to 20 carbon atoms, such as hexane, heptane, octane, nonane and decane; isoparaffins such as isooctane; n-alkylbenzenes having an aliphatic chain of 5 to 15 carbon atoms, such as pentylbenzene, hexylbenzene, heptylbenzene and octylbenzene; isoalkylbenzenes such as cumene; alicyclic hydrocarbons such as cyclohexane; aliphatic ethers such as dihexyl ethers; aromatic esters such as dibutyl phthalate; aliphatic esters such as ethyl decanoate; and silicone oils such as polydimethylsiloxane.

The reaction solvent used is not limited to a single solvent, but may be a mixed solvent system comprising two or more solvents selected with consideration for the solubility of the raw materials and the product, their toxicity to microorganisms, or the like.

One specific example of the interface bioreactor is one using a reaction solvent comprising a paraffin and immobilizing carriers comprising polyvinyl alcohol-coated filter pads packed in a reaction tank so as to be arranged in a horizontal or vertical position.

Alternatively, the coupling of fermentation and microbial transformation reactions in the present invention can also be achieved according to an aqueous/organic two-phase system reaction method [M. D. Hocknull and M. D. Lilly, Appl. Microbiol. Biotechnol., 33, 148 (1990)] using a liquid medium instead of the hydrophilic immobilizing carriers of the interface bioreactor. In this case, however, the results obtained with the interface bioreactor will not be surpassed because the toxicity of the organic solvent and of the hardly water-soluble alcohol, organic acid or aldehyde used for esterification is manifested.

With regard to the supply of oxygen for microbial growth, when the microorganism is made to perform organic acid fermentation or alcohol fermentation, it is rather desirable to grow the microorganism and carry out the reaction without any oxygen supply (i.e., under anaerobic conditions). However, since the microorganism generally consumes the oxygen present in the reaction solvent during the process of growth, it is not necessarily required to subject the reaction solvent to a treatment such as deaeration or replacement with nitrogen. On the other hand, when the microorganism is made to produce acetyl-CoA, it is preferable to fermentatively produce acetyl-CoA under aerobic conditions. The interface bioreactor is particularly effective for this purpose.

With regard to nutrients necessary for microbial growth, since a water-soluble organic acid, alcohol or acetyl-CoA needs to be produced by fermentation, it is essential that the aqueous medium contain a raw material for fermentative production of the water-soluble organic acid, alcohol or acetyl-CoA. Useful fermentation materials include, for example, saccharides such as glucose, starch and sucrose. In addition to the substrate used for the fermentative production of a water-soluble organic acid, alcohol or acetyl-CoA, the nutrients may include common culture medium components as described, for example, in Japanese Patent Laid-Open No. 91878/'93. By way of example, a typical aqueous medium (or culture medium) is composed of 2 to 5% by weight of glucose, 3% by weight of peptone, 3% by weight of malt extract, 3% by weight of yeast extract, 0.1% by weight of magnesium sulfate ($MgSO_4 \cdot 7H_2O$) and 1 liter of distilled water (pH 6.0).

Generally, the concentration of the saccharide (e.g., glucose) used as the fermentation material in the aqueous medium is suitably in the range of about 3 to 5% by weight, because unduly high concentrations thereof may inhibit microbial growth, enzyme activity and fermentation activity. However, if the concentration of the saccharide in the aqueous medium is increased, microbial oxidation reactions may be inhibited in certain cases. Accordingly, care must be taken when the microbial oxidation reaction of an alcohol or aldehyde dissolved in the hydrophobic organic solvent is utilized. Specifically, when glucose is used, it is desirable to maintain its concentration at 2 to 3% by weight. On the other hand, this phenomenon is important in that, when the process of the present invention is carried out without utilizing such a microbial oxidation reaction, undesired oxidation reactions can be repressed. For example, by increasing the concentration of the saccharide to about 3% by weight or greater, undesirable side reactions (e.g., the oxidative decomposition reaction of the hardly water-soluble alcohol or organic acid contained in the reaction solvent) may often be repressed significantly, resulting in a marked improvement in the yield of the ester. Accordingly, it is desirable to determine the optimum addition concentration of the saccharide experimentally in particular cases.

When an organic acid produced by microbial oxidation of the alcohol or aldehyde dissolved in the hydrophobic organic solvent is utilized for an esterification reaction with the fermentation product, high concentrations of the saccharide (e.g., glucose) used as the fermentation material may inhibit the alcohol dehydrogenase or aldehyde dehydrogenase. Accordingly, the saccharide contained in the aqueous medium is desirably maintained at such a concentration as not to inhibit the activity of the alcohol dehydrogenase or aldehyde dehydrogenase.

The organic acids produced by organic acid fermentation of the aforesaid saccharides in the present invention include, for example, formic acid, acetic acid, propionic acid, lactic acid, butyric acid and amino acids. The alcohols produced by alcoholic fermentation of the aforesaid saccharides in the present invention include, for example, lower alcohols such as ethanol, propanol and butanol; and diols such as butanediol. According to the present invention, these fermentation products and acetyl-CoA are subjected to a microbial esterification reaction with a hardly water-soluble alcohol or organic acid as described below, or with a hardly water-soluble alcohol or organic acid produced by microbial reduction or oxidation of a hardly water-soluble alcohol or aldehyde.

No particular limitation is placed on the hardly water-soluble alcohol or organic acid contained in the reaction solvent and used for the esterification reaction. Useful examples thereof include medium-chain alkanols such as 1-octanol and 1-decanol; long-chain alkanols such as 1-octadecanol; terpene alcohols such as citronellol, menthol and geraniol; aromatic alcohols such as phenylpropanol and phenylbutanol; alkanoic acids such as octanoic acid and decanoic acid; aromatic acids such as 2-hydroxy-4-phenylbutanoic acid; and terpenic acids such as citronellic acid and geranic acid.

Similarly, no particular limitation is placed on the hardly water-soluble alcohol or aldehyde contained in the reaction solvent and used for the microbial reduction or oxidation, so long as it is soluble in the hydrophobic organic solvent used as the reaction solvent. Useful examples of the hardly water-soluble alcohol include the above-enumerated alcohols, and useful examples of the hardly water-soluble aldehyde include alkanals such as octanal and decanal; terpene aldehydes such as citronellal and geranyl aldehyde; and aromatic aldehydes such as phenylpropanal and phenylbutanal.

Generally, on the basis of the toxicity alleviation phenomenon in the interface bioreactor, the addition amount of the hardly water-soluble alcohol, organic acid or aldehyde can be determined so as to give a high concentration. However, the addition amount thereof is also affected by the species of the microorganism and the polarity of the raw materials. For example, since terpene alcohols (e.g., citronellol) and medium-chain alkanols (e.g., 1-octanol) cause damage especially to the pathways for the production of water-soluble alcohols, organic acids and acetyl-CoA, their toxicity cannot be substantially avoided even with the aid of the interface bioreactor. Depending on the species of the microorganism, they may be added at a concentration of as low as 1 to 4%. In such a case, this problem can be solved by adding the terpene alcohol or alkanol used as a raw material according to the successive addition method (or the fed-batch addition method).

Even organic acids and alcohols having relatively high solubility in water can be used as substrates for esterification in the present invention, provided that their addition concentration in the reaction solvent is kept sufficiently low and they are gradually added according to the fed-batch addition method.

In cases where a hardly water-soluble alcohol or organic acid produced by microbial oxidation of a hardly water-soluble alcohol or by microbial reduction or oxidation of a hardly water-soluble aldehyde is utilized for the purpose of esterification in the process of the present invention, the employment of microbial reduction or oxidation may be decided according to the water-soluble organic acid, alcohol or acetyl-CoA produced by fermentation. More specifically, when a water-soluble organic acid or acetyl-CoA is accumulated as a result of fermentation, it is preferable to produce an alcohol by microbial reduction of an aldehyde. On the other hand, when a water-soluble alcohol is produced by fermentation, it is preferable to produce a hardly water-soluble organic acid by microbial oxidation of a hardly water-soluble alcohol. Although it is sufficiently possible to microbially oxidize an aldehyde to an organic acid, the reduction reaction may proceed more rapidly in such a case.

No particular limitation is placed on the species of the microorganism used in the present invention, provided that it has the activity of producing a water-soluble organic acid, alcohol or acetyl-CoA by fermentation of a saccharide (i.e., organic acid fermentation activity, alcohol fermentation activity or acetyl-CoA fermentation activity), the ability to produce a lipase, an esterase or an alcohol acetyltransferase, and if appropriate, the ability to reduce a hardly water-soluble aldehyde dissolved in the reaction solvent of the interface bioreactor or oxidize a hardly water-soluble alcohol or aldehyde dissolved therein. Useful microorganisms include, for example, bacteria of the genera Propionibacterium, Acetobacter, Lactobacillus, Pseudomonas and Bacillus; yeasts of the genera Issatchenkia, Hansenula, Candida, Saccharomyces, Kluyberomyces and Pichia; and molds of the genera Rhizopus, Aspergillus and Penicillium. More specifically, they include, for example, *Propionibacterium shermanii, Acetobacter aceti, Lactobacillus brevis, Pseudomonas fluorescens, Hansenula saturnus, Hansenula anomala, Candida utilis, Issatchenkia terricola, Bacillus subtilis* subsp. *niger, Saccharomyces cerevisiae, Pichia heedii, Pichia quercuum, Rhizopus delemar, Aspergillus terreus* and *Penicillium notaum*. Especially when microorganisms capable of producing a lipase or esterase having excellent stereoselectivity (e.g., microorganisms of the genera Pseudomonas, Candida and Aspergillus) are used, the microbial esterification reaction proceeds stereoselectively depending on the type of the alcohol or organic acid contained in the reaction solvent.

Such a microorganism can be attached to the above-described hydrophilic immobilizing carrier, for example, by impregnating the hydrophilic immobilizing carrier with an aqueous medium (or culture medium) containing nutrients including the above-described saccharide as an essential component, inoculating it with the desired microorganism, and cultivating the microorganism under the optimum conditions for about 0 to 5 days.

The hydrophilic immobilizing carrier having the microorganism attached thereto in the above-described manner is supplied with an aqueous medium containing nutrients, if necessary, and brought into contact with a hydrophobic solvent having dissolved therein a hardly water-soluble alcohol, organic acid or aldehyde according to the properties of the microorganism. Thereafter, the cultivation is continued until the resulting ester is fully accumulated. The cultivation temperature employed therefor may be a temperature favorable to the microorganism used (e.g., an optimum temperature between about 20° C. and about 40° C.).

The ester accumulated at high concentrations in the reaction solvent can be recovered according to any of common separation and purification techniques including, for example, a step involving concentration by distilling off the reaction solvent, and a method for separation by adsorbing the resulting ester to an adsorbent such as silica gel or alumina.

The present invention is more specifically explained with reference to the following examples. However, these examples are not to be construed to limit the scope of the invention.

EXAMPLE 1

200 ml of an agar plate medium (pH 6.0) composed of 5 g of peptone, 3 g of yeast extract, 3 g of malt extract, 1 g of magnesium sulfate, 40 g of glucose, 20 g of agar and 1 liter of distilled water was poured into a Petri dish made of glass and having a diameter of 21 cm. Using Conradi's rod, this agar medium was inoculated with 2 ml of a one-day culture of *Hansenula saturnus* IFO 0809. After the microorganism was grown overnight in standing culture, 70 ml of a 2% citronellol solution in decane was placed over the agar medium and a fermentation-transformation test was carried out for 5 days. As a result of gas chromatographic analysis of the decane layer, an accumulation of citronellyl acetate in the decane layer was recognized from one day after the start of the reaction, and its accumulation concentration reached 18 g/l on the fifth day.

EXAMPLE 2

The internal voids of filter pads (6 cm×13 cm) coated with a gel of 10% polyvinyl alcohol (ENTV-500; manufactured by Kansai Paint Co., Ltd.) were filled with a liquid medium having the same composition as described in Example 1. Thirteen plate-like carriers prepared as above were inoculated with a one-day culture of *Pichia heedii* IFO 10019, grown for a day, and then packed in a stainless steel tank having an internal capacity of 3 liters by fixing them to a stainless steel frame in a vertical position.

One liter of a 3% geraniol solution in undecane was charged thereinto and reacted for 5 days under agitation with a magnetic stirrer installed at the bottom of the reactor. As a result of gas chromatographic analysis of the undecane layer, a significant accumulation of geranyl acetate in the decane layer was recognized from one day after the start of the reaction, and its accumulation concentration reached 26 g/l on the fifth day.

EXAMPLE 3

An agar plate medium having the same composition as described in Example 1 was poured into a Petri dish made of glass and having a diameter of 21 cm. Using Conradi's rod, this agar medium was inoculated with 2 ml of a one-day culture of *Issatchenkia terricola* IFO 0933. After the microorganism was grown overnight in standing culture, 70 ml of a 2% decanoic acid solution in decane was placed over the agar medium and a fermentation-transformation test was carried out for 5 days. As a result of gas chromatographic analysis of the decane layer, an accumulation of ethyl decanoate in the decane layer was recognized from one day after the start of the reaction, and its accumulation concentration reached 9 g/l on the fifth day.

EXAMPLE 4

An agar plate medium having the same composition as described in Example 1 was poured into a Petri dish made of glass and having a diameter of 21 cm. Using Conradi's rod, this agar medium was inoculated with 2 ml of a one-day culture of *Bacillus subtilis* subsp. *niger* IFO 3108. After the microorganism was grown overnight in standing culture, 70 ml of a 1% menthol solution in decane was placed over the agar medium and a fermentation-transformation test was carried out for 5 days. As a result of gas chromatographic analysis of the decane layer, an accumulation of ethyl decanoate in the decane layer was recognized from one day after the start of the reaction, and its accumulation concentration reached 6 g/l on the fifth day.

EXAMPLE 5

200 ml of an agar plate medium (pH 6.0) composed of 5 g of peptone, 3 g of malt extract, 1 g of magnesium sulfate, 40 g of glucose, 20 g of agar and 1 liter of distilled water was poured into a Petri dish made of glass and having a diameter of 21 cm. Using Conradi's rod, this agar medium was inoculated with 2 ml of a one-day culture of *Hansenula saturnus* IFO 0809. After the microorganism was grown overnight in standing culture, 70 ml of a 2% citronellal solution in decane was placed over the agar medium and a fermentation-transformation test was carried out in shaking culture for 5 days. As a result of gas chromatographic analysis of the decane layer, the microbial esterification reaction of citronellol formed by microbial reduction of citronellal with acetic acid formed by acetic acid fermentation was observed, and an accumulation of citronellyl acetate in the decane layer was recognized from one day after the start of the reaction. In consequence of the fermentation-transformation test carried out for 5 days, the accumulation concentration of citronellyl acetate in the decane layer reached 19 g/l.

EXAMPLE 6

The internal voids of filter pads (6 cm×13 cm) coated with a gel of 10% polyvinyl alcohol (ENTV-500; manufactured by Kansai Paint Co., Ltd.) were filled with a liquid medium having the same composition as described in Example 5. Thirteen plate-like carriers prepared as above were inoculated with a one-day culture of *Pichia quercuum* IFO 0949, grown for a day, and then packed in a stainless steel tank having an internal capacity of 3 liters by fixing them to a stainless steel frame in a vertical position.

One liter of a 3% geranyl aldehyde solution in undecane was charged thereinto and reacted for 5 days under agitation with a magnetic stirrer installed at the bottom of the reactor. As a result of gas chromatographic analysis of the undecane layer, the microbial esterification reaction of geraniol formed by microbial reduction of geranyl aldehyde with acetic acid formed by acetic acid fermentation was observed. The accumulation concentration of geranyl acetate in the undecane layer reached 28 g/l on the fifth day.

EXAMPLE 7

An agar plate medium having the same composition as described in Example 5 was poured into a Petri dish made of glass and having a diameter of 21 cm. Using Conradi's rod, this agar medium was inoculated with 2 ml of a one-day culture of *Issatchenkia terricola* IFO 0933. After the microorganism was grown overnight in standing culture, 70 ml of a 3% decanol solution in decane was placed over the agar medium and a fermentation-transformation test was carried out for 5 days. As a result of gas chromatographic analysis of the decane layer, an accumulation of ethyl decanoate which was the esterification product of decanoic acid formed by microbial oxidation of decanol with ethanol formed by ethanol fermentation was recognized, and its accumulation concentration reached 10 g/l on the fifth day.

What is claimed is:

1. A coupled microbial fermentation and esterification process for producing an esterified fermentation product from a saccharide which comprises:

attaching a microorganism having (a) organic acid fermentation activity, alcohol fermentation activity or acetylcoenzyme A fermentation activity and (b) an esterase production ability or an alcohol acetyltransferase production ability to a hydrophilic immobilizing carrier, contacting the microorganism on the carrier with a hydrophobic organic solvent containing at least one compound selected from the group consisting of water-insoluble or slightly water-soluble alcohols, organic acids and aldehydes while in the presence of an aqueous medium containing a saccharide, growing the microorganism at a contact interface between the hydrophobic organic solvent and the aqueous medium to fermentatively produce from the saccharide through the fermentation activity of the microorganism a fermentation product of water soluble organic acid, alcohol or acetylcoenzyme A, and subjecting, at the time of said production, the fermentation product of water soluble organic acid, alcohol or acetylcoenzyme A to a microbial esterification reaction using the esterase or alcohol acetyltransferase produced by the microorganism with (a) the water-insoluble or slightly water-soluble alcohol or organic acid contained in the hydrophobic organic solvent, (b) a water-insoluble or slightly water-soluble organic acid product produced by microbial oxidation of the water-insoluble or slightly water-soluble alcohol contained in the hydrophobic organic solvent, or (c) a water-insoluble or slightly water-soluble alcohol or organic acid product produced by microbial reduction or oxidation of the water-insoluble or slightly water-soluble aldehyde contained in the hydrophobic organic solvent, to form the esterified fermentation product from the saccharide.

2. A process as claimed in claim 1 wherein the microorganism is selected from the group consisting of *Propionibacterium shermanii, Acetobacter aceti, Lactobacillus brevis, Pseudomonas fluorescens, Hansenula saturnus, Hansenula anomala, Pichia heedii, Pichia quercuum, Candida utilis, Issatchenkia terricola, Bacillus subtilis* subsp. *niger, Saccharomyces cerevisiae, Rhizopus delemar, Aspergillus terreus* and *Penicillium notaum*.

3. A process as claimed in claim 1 wherein the saccharide is selected from the group consisting of glucose, starch and sucrose.

4. A process as claimed in claim 1 wherein the hydrophobic organic solvent is selected from the group consisting of normal paraffins, liquid paraffins, isoparaffins, n-alkylbenzenes, isoalkylbenzenes, alicyclic hydrocarbons and aliphatic ethers.

5. A process as claimed in claim 1 wherein the water-insoluble or slightly water-soluble alcohol is selected from the group consisting of long-chain or medium-chain alkanols, terpene alcohols and aromatic alcohols.

6. A process as claimed in claim 1 wherein the water-insoluble or slightly water-soluble organic acid is selected from the group consisting of alkanoic acids, aromatic acids and terpene acids.

7. A process as claimed in claim 1 wherein the water-insoluble or slightly water-soluble aldehyde is selected from the group consisting of alkanals, terpene aldehydes and aromatic aldehydes.

8. A process as claimed in claim 1 wherein the fermentatively produced water-soluble organic acid is formic acid, acetic acid, propionic acid, lactic acid, butyric acid or an amino acid.

9. A process as claimed in claim 1 wherein the fermentatively produced water-soluble alcohol is ethanol, propanol, butanol or butanediol.

10. A process as claimed in claim 1 wherein the microbial esterification reaction is the esterification reaction of the fermentatively produced water-soluble organic acid with (a) the water-insoluble or slightly water-soluble alcohol contained in the hydrophobic organic solvent, or (b) the water-insoluble or slightly water-soluble alcohol product produced by microbial reduction of the water-insoluble or slightly water-soluble aldehyde contained in the hydrophobic organic solvent.

11. A process as claimed in claim 1 wherein the microbial esterification reaction is the esterification reaction of the fermentatively produced water-soluble alcohol with (a) the water-insoluble or slightly water-soluble organic acid contained in the hydrophobic organic solvent, or (b) the water-insoluble or slightly water-soluble organic acid product produced by microbial oxidation of the water-insoluble or slightly water-soluble alcohol contained in the hydrophobic organic solvent or (c) the water-insoluble or slightly water-soluble organic acid product produced by microbial oxidation of the water-insoluble or slightly water-soluble aldehyde contained in the hydrophobic organic solvent.

12. A process as claimed in claim 1 wherein the microbial esterification reaction is the esterification reaction of the fermentatively produced acetylcoenzyme A with (a) the water-insoluble or slightly water-soluble alcohol contained in the hydrophobic organic solvent, or with (b) the water-insoluble or slightly water-soluble alcohol product produced by microbial reduction of the water-insoluble or slightly water-soluble aldehyde contained in the hydrophobic organic solvent.

13. A process as claimed in claim 1 wherein the esterase production ability is a lipase production ability and wherein the esterase is a lipase.

14. A process as claimed in claim 1 wherein the esterification product is an organic acid ester.

* * * * *